US008530691B2

(12) United States Patent
Mantegazza et al.

(10) Patent No.: US 8,530,691 B2
(45) Date of Patent: Sep. 10, 2013

(54) PROCESS FOR THE PREPARATION OF FESOTERODINE

(75) Inventors: Simone Mantegazza, Milan (IT); Pietro Allegrini, San Donato Milanese (IT); Emanuele Attolino, Palagiano (IT)

(73) Assignee: Dipharma Francis s.r.l., Baranzate (IT)

( * ) Notice: Subject to any disclaimer, the term of this patent is extended or adjusted under 35 U.S.C. 154(b) by 334 days.

(21) Appl. No.: 12/914,316

(22) Filed: Oct. 28, 2010

(65) Prior Publication Data

US 2011/0105783 A1   May 5, 2011

(30) Foreign Application Priority Data

Oct. 29, 2009   (IT) .............................. MI2009A1882

(51) Int. Cl.
*C07C 229/00*   (2006.01)
(52) U.S. Cl.
USPC .......................................................... 560/42
(58) Field of Classification Search
USPC .......................................................... 560/42
See application file for complete search history.

(56) References Cited

U.S. PATENT DOCUMENTS

| 6,713,464 B1 | 3/2004 | Meese et al. | |
| 6,858,650 B1* | 2/2005 | Meese | 514/530 |
| 2003/0199582 A1 | 10/2003 | Hawley | |
| 2008/0076927 A1* | 3/2008 | By et al. | 546/137 |

FOREIGN PATENT DOCUMENTS

| EP | 0 957 073 A1 | 11/1999 |
| EP | 1927585 A2 | 6/2008 |
| EP | 2281801 A1 | 2/2011 |
| WO | 94/11337 A1 | 5/1994 |
| WO | 01/96279 A1 | 12/2001 |
| WO | 2007/138440 A1 | 12/2007 |
| WO | 2007/140986 A1 | 12/2007 |
| WO | 2007/144091 A1 | 12/2007 |
| WO | 2007/147547 A1 | 12/2007 |
| WO | WO 2011/012584 A1 * | 2/2011 |

OTHER PUBLICATIONS

De Castro et al., "Selective Nosylation of 1-Phenylpropane-1,3-diol and Perchloric Acid Mediated Friedel-Crafts Alkylation: Key Steps for the New and Straightforward Synthesis of Tolterodine", Synthesis, 2008, No. 12, pp. 1841-1844.
U.S. Appl. No. 13/295,224, Marco Artico, et al., filed Nov. 14, 2011.

* cited by examiner

*Primary Examiner* — Johann R Richter
*Assistant Examiner* — Blaine G Doletski
(74) *Attorney, Agent, or Firm* — Rothwell, Figg, Ernst & Manbeck, P.C.

(57) ABSTRACT

A process for the preparation of (R)-2-(3-diisopropylamino-1-phenylpropyl)-4-(hydroxymethyl)-phenol isobutyrate (Fesoterodine), its (S)-enantiomer, and novel intermediates useful in the synthesis.

15 Claims, No Drawings

PROCESS FOR THE PREPARATION OF FESOTERODINE

FIELD OF THE INVENTION

The invention relates to a process for the preparation of (R)-2-(3-diisopropylamino-1-phenylpropyl)-4-(hydroxymethyl)-phenol isobutyrate (Fesoterodine), its (S)-enantiomer and novel intermediates useful in its synthesis.

TECHNOLOGICAL BACKGROUND

Fesoterodine, namely (R)-2-(3-diisopropylamino-1-phenylpropyl)-4-(hydroxymethyl)-phenol isobutyrate, of formula (I)

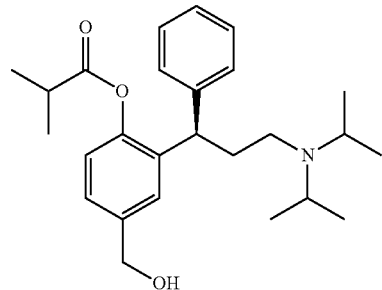

(I)

is a known compound with antimuscarinic activity, clinically used as the fumarate, for the treatment of the hyperactive bladder syndrome and particularly of urinary incontinence.

U.S. Pat. No. 6,713,464 discloses the preparation of Fesoterodine through different synthetic methods, as reported e.g. in the Scheme hereinbelow.

Scheme

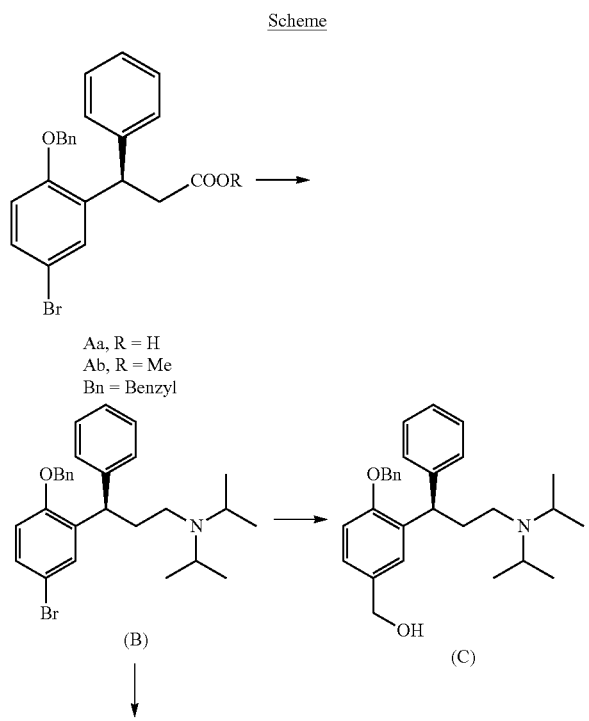

Aa, R = H
Ab, R = Me
Bn = Benzyl

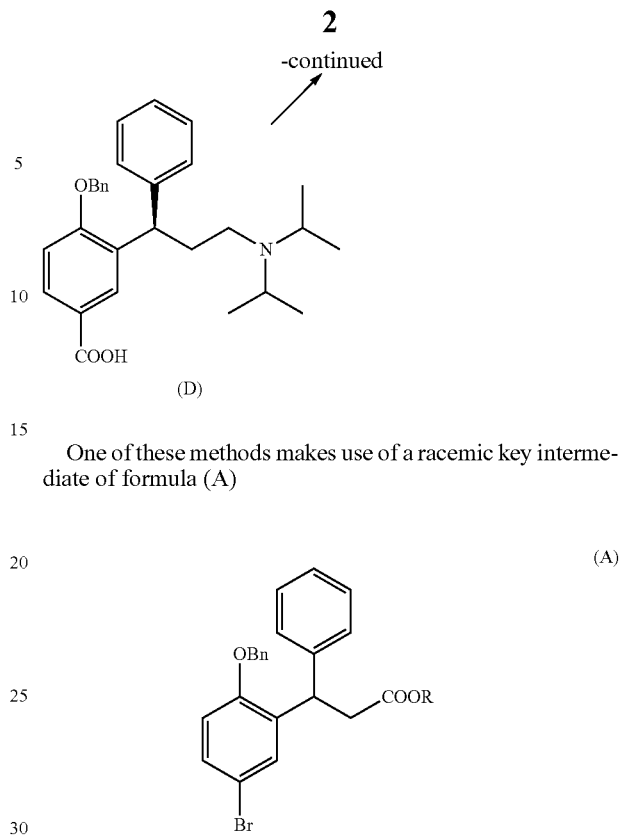

One of these methods makes use of a racemic key intermediate of formula (A)

(A)

obtainable in three steps from 4-bromophenol. After resolution, through formation of the diastereomeric salts, the methylpropionic side chain of the optically active compound of formula (Ab) is transformed into the diisopropylamine side chain of the compound of formula (B).

Compound (C) is obtained, through C-1 homologation of the Grignard reagent of compound of formula (B) with solid $CO_2$, to afford compound (D), that is subsequently reduced with $LiAlH_4$. This step was optimized in WO 2007/144091, as reported in the above Scheme, by directly reacting the Grignard reagent of compound (B) with paraformaldehyde or trioxane. Compound (C) is then converted to Fesoterodine upon debenzylation and selective esterification of the resulting phenol compound.

As it can be noted, these processes are quite long lasting and complex, and require protective groups for the phenol hydroxyl group, thus involving an increase in number of steps and negatively affecting both yields and industrialization of the process.

There is therefore the need for an alternative synthesis which provides Fesoterodine or a salt thereof with high purity, from low cost starting materials and with an efficient process that can be reproduced on an industrial scale.

SUMMARY OF THE INVENTION

A process has now been found which provides Fesoterodine, its (S)-enantiomer or a salt thereof from low cost starting materials, with few synthetic steps and in high purity. The process of the invention is therefore more advantageous than known methods.

DETAILED DISCLOSURE OF THE INVENTION

The invention relates to a process for the preparation of a compound of formula (IIa) or (IIb), or a salt thereof

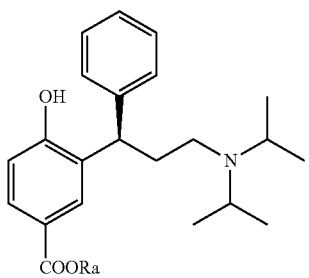

(IIa)

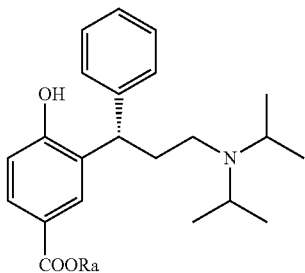

(IIb)

wherein Ra is $C_1$-$C_6$ alkyl,
comprising the resolution of the corresponding racemic compound of formula (II)

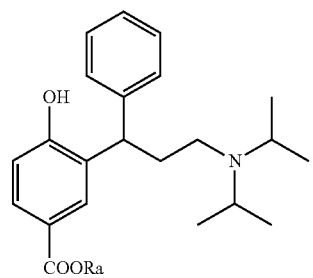

(II)

wherein Ra is as defined above,
through formation of a diastereomeric salt thereof with an optically active organic acid.

A salt of a compound of formula (IIa) or formula (IIb) is preferably a pharmaceutically acceptable salt thereof.

A $C_1$-$C_6$ alkyl group, which may be a straight or branched group, is for example a $C_1$-$C_4$ alkyl group, preferably methyl, ethyl or isopropyl, in particular methyl.

An optically active organic acid can be an optically active carboxylic or sulfonic acid.

An optically active carboxylic acid can be selected for example from (+) or (−) tartaric acid, (+) or (−) 2,3-dibenzoyltartaric acid, mandelic acid, 3-chloro mandelic acid and abietic acid; a sulfonic acid is for example S-(+)-camphorsulfonic acid.

The resolution reaction of the diastereomeric salts can be carried out in a solvent, selected for example from water, a dipolar aprotic solvent, typically dimethylformamide, dimethylacetamide, acetonitrile, dimethylsulfoxide; a $C_3$-$C_8$ ketone, typically acetone, methyl ethyl ketone, methyl isobutyl ketone; a cyclic or acyclic ether, typically tetrahydrofuran, dioxane or methyl-tert.butyl ether; an ester, typically ethyl acetate, isopropyl acetate, butyl acetate; a chlorinated solvent, typically dichloromethane; a polar protic solvent, such as a straight or branched $C_1$-$C_6$ alkanol, for example a $C_1$-$C_4$ alkanol, typically methanol, ethanol, isopropanol or butanol; or a mixture of two or more, typically two, of said solvents. The resolution reaction can be preferably carried out in a $C_1$-$C_6$ alkanol, for example a $C_1$-$C_4$ alkanol, typically methanol, ethanol, isopropanol or butanol.

The diastereomeric salt of a compound (IIa) or (IIb) can be separated, for example by crystallization from the reaction mixture, recovered and then cleaved to afford the compound of formula (IIa) or (IIb), respectively. The separation, recovery and cleavage of the salt can be carried out according to known techniques. A compound of formula (IIa) or (IIb) has high enantiomeric purity. The enantiomeric purity of a isolated (IIa) or (IIb) enantiomer or of a salt thereof, calculated by chiral HPLC and expressed in terms of enantiomeric ratio, is typically equal to or higher than 95:5, preferably equal to or higher than 99:1.

A compound of formula (IIa) or (IIb) can be converted into a salt thereof, typically a pharmaceutically acceptable salt, by known methods, for example by treatment with an inorganic acid, such as hydrochloric or sulfuric acid, or with an organic acid, such as fumaric or succinic acid. Similarly, a salt of a compound of formula (IIa) or (IIb) can be converted into the free base according to known methods.

The recovery of a salt of a compound of formula (IIa) or (IIb) can be carried out by known procedures, for example by filtration.

A compound of formula (IIa) or of formula (IIb) can then be converted into Fesoterodine, or its (S)-enantiomer, respectively, or a pharmaceutically acceptable salt thereof, by a process comprising:

a) the reduction of the carboxylate group in a compound of formula (IIa) or of formula (IIb), or a salt thereof, to obtain a compound of formula (IIIa) or (IIIb), respectively, or a salt thereof,

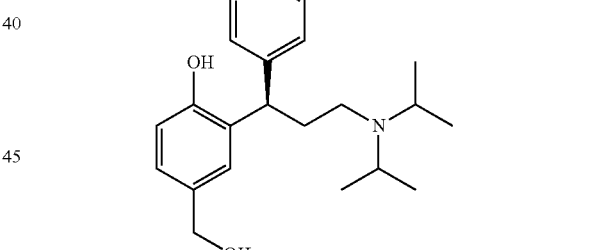

(IIIa)

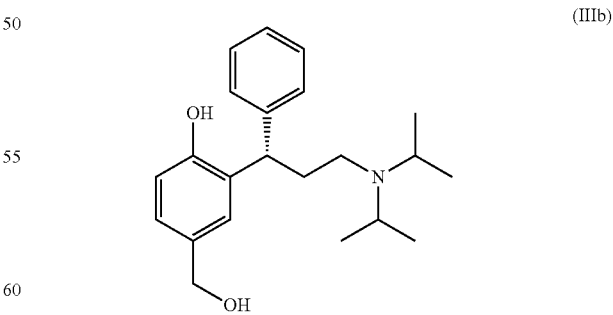

(IIIb)

b) the esterification of the phenol hydroxyl group in the compound of formula (IIIa) or (IIIb), or a salt thereof, to obtain Fesoterodine or its (S)-enantiomer, respectively, or a salt thereof; and, if desired, the conversion of Fesoterodine or its (S)-enantiomer into a salt thereof, or the cleavage of a salt of Fesoterodine or of its (S)-enantiomer into free Fesoterodine or its free (S)-enantiomer, respectively.

A salt of a compound of formula (IIIa) or formula (IIIb) is preferably a pharmaceutically acceptable salt thereof.

The reduction and esterification reactions can be carried out according to known procedures, for example according to U.S. Pat. No. 6,713,464.

The conversion of Fesoterodine or its (S)-enantiomer into a salt thereof, in particular a pharmaceutically acceptable salt thereof, can be effected by known methods, for example by treatment with an inorganic acid, such as hydrochloric or sulfuric acid, or with an organic acid, such as fumaric or succinic acid.

The recovery of the resulting salt can be carried out by known procedures, for example by filtration.

Analogously, the conversion of a salt of Fesoterodine or of its (S)-enantiomer into free Fesoterodine or its free (S)-enantiomer, respectively, can be carried out according to known methods.

The acylation reaction of the phenol hydroxyl in intermediates of formulae (IIIa) and (IIIb), when conducted according to known techniques, is not enough regioselective, due to the presence of the primary hydroxy function.

The Applicant has found novel methods to carry out the esterification reaction of the phenol hydroxyl group of a compound of formula (IIIa) or of formula (IIIb), which are more selective than the known ones.

Therefore, according to a preferred embodiment of the invention, the esterification of the phenol hydroxyl group in a compound of formula (IIIa) or (IIIb), as defined above, can be carried out by a process comprising:
  a) the treatment of a compound of formula (IIIa) or (IIIb), respectively, or a salt thereof, with an acylating agent under phase-transfer reaction conditions; or
  b) the treatment of a compound of formula (IVa) or (IVb), respectively, with an acylating agent,

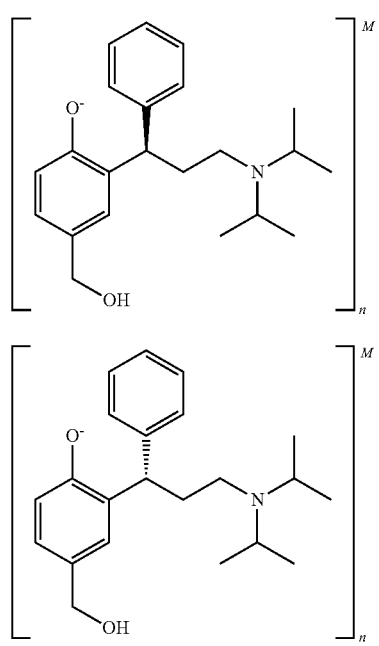

wherein M is an organic cation or an alkali or alkaline-earth metal cation; and n is 1 or 2.

An acylating agent, as herein defined, can be a isobutyryl halide, preferably isobutyryl chloride; or isobutyric anhydride.

The phase-transfer conditions can for example be attained by contacting an organic solution, obtained dissolving the acylating agent and a compound of formula (IIIa) or (IIIb), respectively, or a salt thereof, in a substantially water-immiscible organic solvent, with a solution of an alkali or alkaline-earth metal hydroxide, phosphate or carbonate in water or a water/$C_1$-$C_4$ alkanol mixture, for example methanol or ethanol.

A substantially water-immiscible organic solvent can for example be a $C_3$-$C_8$ ketone, preferably methyl-isobutyl-ketone; a cyclic or acyclic ether, typically methyl-tert.butyl ether; an ester, typically ethyl acetate, isopropyl acetate, butyl acetate; a chlorinated solvent, typically dichloromethane; or an aromatic hydrocarbon, typically toluene.

A salt of formula (IVa) or (IVb) can be obtained by treatment of a compound of formula (IIIa) or (IIIb), respectively, with a strong base, e.g. a hydroxide, carbonate or phosphate of an alkali or alkaline-earth metal, preferably sodium, potassium or calcium, or a $C_1$-$C_{12}$ alkylammonium quaternary salt, preferably a tetrabutylammonium salt.

The reaction of a salt of formula (IVa) or (IVb) with an acylating agent can optionally be effected in the presence of a solvent.

A solvent can for example be selected from water, a dipolar aprotic solvent, typically dimethylformamide, dimethylacetamide, acetonitrile, dimethylsulfoxide; a $C_3$-$C_8$ ketone, typically acetone, methyl ethyl ketone, methyl isobutyl ketone; a cyclic or acyclic ether, typically tetrahydrofuran, dioxane or methyl-tert.butyl ether; a chlorinated solvent, typically dichloromethane; or a mixture of two or more, typically two, of said solvents. Said solvent is preferably dimethylacetamide or acetonitrile.

A compound of formula (II), or a salt thereof, can be prepared for example by a process comprising the reaction of a compound of formula (V)

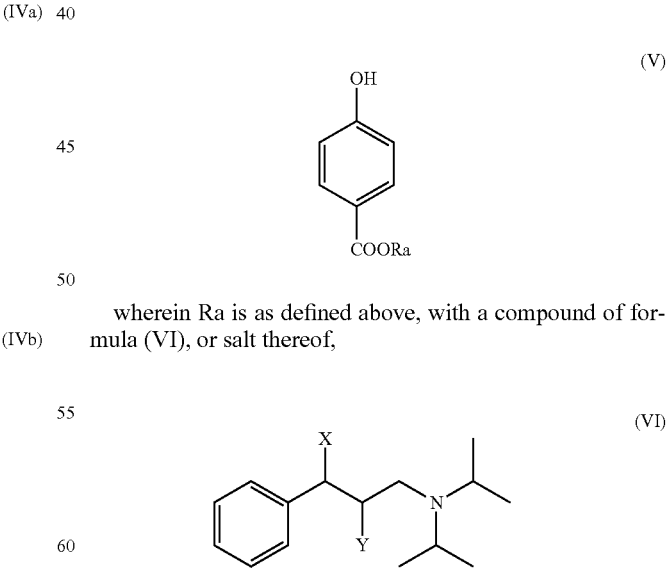

wherein Ra is as defined above, with a compound of formula (VI), or salt thereof, wherein X is a group capable of generating a benzyl carbocation and Y is hydrogen, or X and Y, taken together, form a double bond; in the presence of a strong acid.

X as a group capable of generating a benzyl carbocation is for example a hydroxy group or a reactive derivative thereof, such as a $C_1$-$C_6$ alkyl ether or aryl ether, a $C_1$-$C_6$ alkylcarboxylate or aryl carboxylate, a $C_1$-$C_6$ alkylsulfonate or aryl sulfonate, a trifluoromethanesulfonate, a sulfate, nitrate or phosphate; or a halogen, for example chlorine, bromine or iodine.

A strong acid, as herein defined, can be a strong protic acid or a Lewis acid, wherein a strong protic acid is selected for example from hydrochloric, sulfuric, hydrobromic, perchloric, polyphosphoric, trifluoroacetic, methanesulfonic, p-toluenesulfonic and trifluoromethanesulfonic acids, preferably methanesulfonic acid; a Lewis acid can be selected from $AlCl_3$, $FeCl_3$ and $BF_3$ etherate.

When X is a hydroxy group or a $C_1$-$C_6$ alkylether or aryl ether and Y is hydrogen, or when X and Y, taken together, form a double bond, the strong acid is preferably protic; whereas when X is a halogen atom and Y is hydrogen, the strong acid is preferably a Lewis acid.

Alternatively, a compound of formula (II) or a salt thereof can be prepared by treatment of a compound of formula of formula (VII) with a strong acid

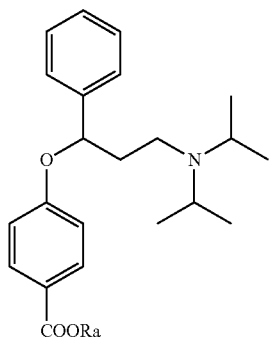

(VII)

wherein Ra is as defined above; preferably in the presence of a compound of formula (V).

The reaction of a compound of formula (V) with a compound of formula (VI) or the conversion of a compound of formula (VII) into a compound of formula (II) can be optionally carried out in the presence of a solvent.

A solvent can be for example an aromatic hydrocarbon such as toluene; a chlorinated solvent such as dichloromethane or chlorobenzene; or a mixture of two or more, typically two or three, of said solvents; or a mixture of one or more, typically two or three, of said solvents with water.

Furthermore, an excess of the strong acid itself can be used as the solvent.

The amount of strong acid used with respect to compounds of formulae (VI) or (VII) is at least stoichiometric, and preferably in excess.

The reaction can be carried out at temperatures ranging from about 0° C. to the reflux temperature of the mixture. When the strong acid is methanesulfonic acid, preferably the temperature approximately ranges from 45° C. to 65° C.

The molar ratio of a compound of formula (V) to a compound of formula (VI), or a salt thereof, or of a compound of formula (VII) to a compound of formula (V), typically can range from 1:1 to 8:1, preferably approximately from 3:1 to 5:1.

A salt of a compound of formula (II) or (VI) is preferably a pharmaceutically acceptable salt thereof.

A compound of formula (II) or (VI) can be converted into a salt thereof by known methods, as reported above. Similarly, a salt of a compound of formula (II) or (VI) can be converted into the free base according to known methods.

The esters of formula (V) are commercially available or can be prepared from the corresponding acid by well known processes, whereas a compound of formula (VI) can be prepared according to what reported in *Synthesis* 2008, 12, 1841-44.

The compounds of formula (VII), which are novel and are a further object of the invention, can be prepared for example according to the synthetic scheme reported hereinbelow.

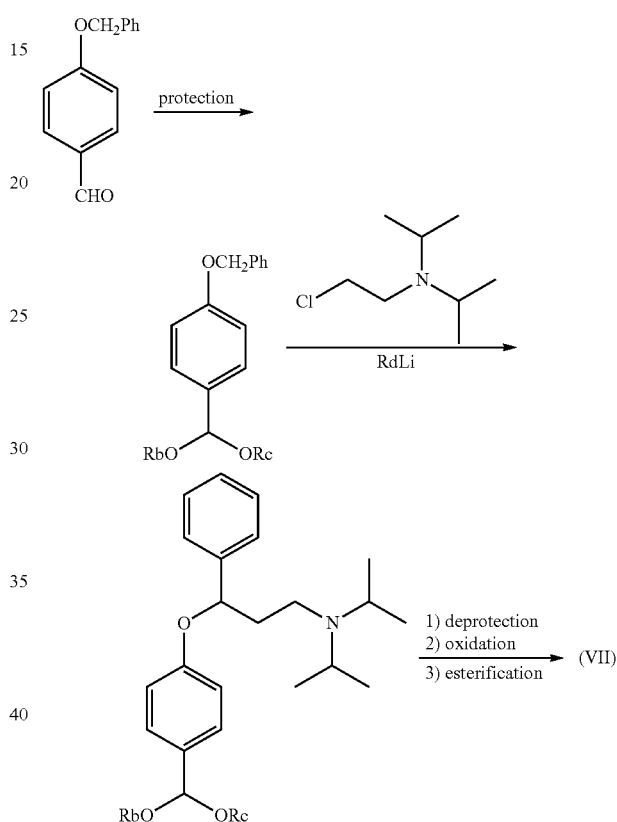

The aldehyde function of p-benzyloxybenzaldehyde, which is commercially available, can be protected for example as the acetal according to known procedures, preferably by acid catalyzed reaction with an alcohol or diol. The protected derivative can be subsequently alkylated using a commercially available diisopropylaminoethyl derivative, in the presence of a strong base, for example an alkyllithium, preferably butyl- or hexyl lithium, and optionally of a solvent, for example tetrahydrofurane. The resulting protected alkyl aryl ether can then be deprotected at the aldehyde function, for example by acid hydrolysis, and the resulting free aldehyde can be oxidized to carboxylic acid, which upon esterification with a $C_1$-$C_6$-alkanol affords compound (VII). Both the oxidation and esterification reactions can be carried out according to one of many known methods.

A further object of the invention is a method for preparing Fesoterodine and its (S)-enantiomer, or a salt thereof, which comprises utilizing as starting material a compound of formula (IIa) or (IIb), or a salt thereof

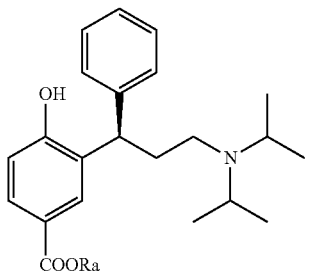

(IIa)

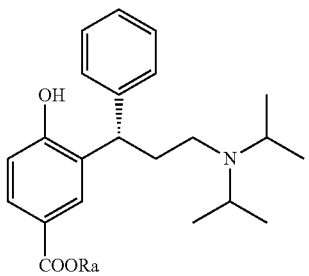

(IIb)

wherein Ra is $C_1$-$C_6$ alkyl, which is obtained by the resolution of the corresponding racemic compound of formula (II)

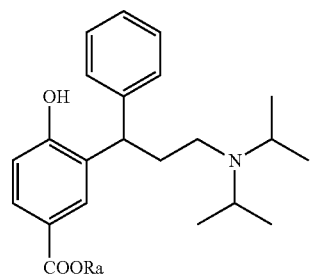

(II)

wherein Ra is as defined above, through formation of a diastereomeric salt thereof with an optically active organic acid.

(S)-2-(3-diisopropylamino-1-phenylpropyl)-4-(hydroxymethyl)-phenol isobutyrate, which is the (S)-enantiomer of Fesoterodine, or a salt thereof, is a novel compound. It can be used for example as reference standard in a method for evaluating the optical purity of Fesoterodine.

The following examples illustrate the invention.

EXAMPLE 1

Synthesis of methyl 3-(3-diisopropylamino-1-phenyl-propyl)-4-hydroxy-benzoate (Compound of Formula II)

Methyl 4-hydroxy-benzoate (52.0 g, 340 mmol) is suspended in methanesulfonic acid (90 ml) in a round-bottom flask under inert atmosphere and the mixture is heated at a temperature of 50-55° C. 3-Diisopropylamino-1-phenyl-propan-1-ol (20.0 g, 85.0 mmol) is slowly added in about 2 hours and the mixture is reacted while hot for 5-6 hours. The mixture is cooled at room temperature and slowly poured in ice/water (200 g) under strong stirring. The product is extracted with dichloromethane (200 ml) and the organic phase is washed with a 10% sodium hydroxide solution (2×100 ml), then with an ammonium chloride aqueous solution until neutral pH. 28.9 g of a product are obtained in 92% yield.

$^1$H-NMR (300 MHz, CDCl$_3$, 28° C.): δ 7.74 (dd, 1H); 7.50 (d, 1H); 7.34-7.16 (m, 5H); 6.88 (d, 1H); 4.50 (dd, 1H); 3.76 (s, 3H); 3.26 (m, 2H); 2.74 (m, 1H); 2.40 (m, 2H); 2.16 (m, 1H); 1.10 (dd, 12H).

EXAMPLE 2

Preparation of the Diastereomeric Salt of a Compound of Formula (II) with (+)-2,3-dibenzoyl-D-tartaric Acid Racemic methyl 3-(3-diisopropylamino-1-phenyl-propyl)-4-hydroxy-benzoate (22.0 g, 59.5 mmol) is dissolved in ethanol (320 ml) in a round-bottom flask under inert atmosphere at a temperature of about 60° C. and (+)-2,3-dibenzoyl-D-tartaric acid (11.1 g, 31.0 mmol) is added thereto. The mixture is left to spontaneously cool until room temperature for 16-18 hours and the suspended solid is filtered and washed with ethanol (3×25 ml). The product is dried in a static dryer at 50° C. under reduced pressure to afford 20.4 g of the salt with 95:5 R/S enantiomeric ratio as evaluated by chiral HPLC.

$^1$H-NMR (300 MHz, DMSO-d6, 28° C.): δ 7.94 (d, 4H); 7.78 (dd, 1H); 7.64-7.56 (m, 3H); 7.45 (t, 4H); 7.28-7.10 (m, 5H); 6.86 (d, 1H); 5.64 (s, 2H); 4.30 (dd, 1H); 3.75 (s, 3H); 3.40 (m, 2H); 2.75-2.50 (m, 2H); 2.25 (m, 2H); 0.96 (dd, 12H).

EXAMPLE 3

Preparation of the Diastereomeric Salt of a Compound of Formula (II) with (−)-2,3-dibenzoyl-L-tartaric Acid Racemic methyl 3-(3-diisopropylamino-1-phenyl-propyl)-4-hydroxy-benzoate (22.0 g, 59.5 mmol) is dissolved in ethanol (320 ml) in a round-bottom flask under inert atmosphere at a temperature of about 60° C. and (−)-2,3-dibenzoyl-L-tartaric acid (11.1 g, 31.0 mmol) is added thereto. The mixture is left to spontaneously cool until room temperature for 16-18 hours and the suspended solid is filtered and washed with ethanol (3×25 ml). The product is dried in a static dryer at 50° C. under reduced pressure to afford 20.4 g of the salt with 95:5 S/R enantiomeric ratio as evaluated by chiral HPLC.

$^1$H-NMR (300 MHz, DMSO-d6, 28° C.): δ 7.94 (d, 4H); 7.78 (dd, 1H); 7.64-7.56 (m, 3H); 7.45 (t, 4H); 7.28-7.10 (m, 5H); 6.86 (d, 1H); 5.64 (s, 2H); 4.30 (dd, 1H); 3.75 (s, 3H); 3.40 (m, 2H); 2.75-2.50 (m, 2H); 2.25 (m, 2H); 0.96 (dd, 12H).

EXAMPLE 4

Preparation of the Diastereomeric Salt of a Compound of Formula (II) with S-(+)-camphorsulfonic Acid Racemic methyl 3-(3-diisopropylamino-1-phenyl-propyl)-4-hydroxy-benzoate (15.0 g, 40.6 mmol) is dissolved in ethanol (50 ml) in a round-bottom flask under inert atmosphere at a temperature of about 50° C. and S-(+)-camphorsulfonic acid (9.9 g, 42.6 mmol) is added thereto. The mixture is left to spontaneously cool until room temperature for 16-18 hours then further cooled on ice bath for 3-4 hours. The suspended solid is filtered and washed with cold ethanol (3×10 ml), then dried under reduced pressure in a static dryer at a temperature of 50° C., to afford 10.8 g of a salt with 99.8:0.2 R/S enantiomeric ratio as evaluated by chiral HPLC.

EXAMPLE 5

Synthesis of R-(+)-2-(3-diisopropylamino-1-phenyl-propyl)-4-hydroxymethyl-phenol (Compound of Formula IIIa)

Methyl (R)-3-(3-diisopropylamino-1-phenyl-propyl)-4-hydroxy-benzoate salt with (+)-2,3-dibenzoyl-D-tartaric acid (14.5 g, 24.1 mmol) is suspended in a round-bottom flask under inert atmosphere in a mixture of ethyl acetate (100 ml) and sodium bicarbonate saturated solution (100 ml) under strong stirring until disappearance of the solid. The organic phase is separated and the aqueous phase extracted with ethyl acetate (2×50 ml), the combined organic phases are concentrated to a residue. The resulting solid is taken up in tetrahydrofuran (100 ml) and slowly added in about 30 minutes to a suspension of lithium aluminium hydride (2.70 g, 72.3 mmol) in tetrahydrofuran at a temperature of about 20° C. The reaction is kept under stirring for about 3 hours, then cooled to a temperature of −10° C. and an ammonium chloride saturated solution (200 ml) is slowly added. The mixture is left to spontaneously warm until room temperature under stirring for about 30 minutes and the suspended solid is filtered. The phases of the filtered solution are separated and the aqueous phase is extracted with ethyl acetate (2×50 ml). Afterwards the combined organic phases are concentrated to a residue, to afford a pale yellow oil, 7.8 g in 95% yield.

$^1$H-NMR (300 MHz, CDCl$_3$, 28° C.): δ 7.40-7.15 (m, 5H); 7.05 (dd, 1H); 6.88 (d, 1H); 6.74 (d, 1H); 4.50 (dd, 1H); 4.42 (s, 2H); 3.24 (m, 2H); 2.72 (m, 1H); 2.46-2.28 (m, 2H); 2.10 (m, 1H); 1.10 (dd, 12H).

By proceeding analogously, starting from (S)-3-(3-diisopropylamino-1-phenyl-propyl)-4-hydroxy-benzoate salt with (−)-2,3-dibenzoyl-L-tartaric acid (S)-2-(3-diisopropylamino-1-phenyl-propyl)-4-hydroxymethyl-phenol is obtained (a compound of formula (IIIb)).

EXAMPLE 6

Synthesis of isobutyric acid R-(+)-2-(3-diisopropylamino-1-phenyl-propyl)-4-hydroxymethyl-phenyl ester (Fesoterodine)

A sodium hydroxide solution (3.30 g, 81.6 mmol) in water (25 ml) and a solution of R-(+)-2-(3-Diisopropylamino-1-phenyl-propyl)-4-hydroxymethyl-phenol (9.30 g, 27.2 mmol) in toluene (30 ml) are placed in a round-bottom flask under inert atmosphere at room temperature. The reaction mixture is slowly added with a solution of isobutyryl chloride (3.50 g, 32.7 mmol) in toluene (20 ml), under strong stirring. After completion of the reaction, the mixture is left under stirring for a further 10 minutes, the phases are separated and the organic phase is concentrated to a residue, to afford 11.0 g of a pale yellow oil, in 98% yield, and 99% purity by HPLC.

$^1$H-NMR (300 MHz, CDCl$_3$, 28° C.): δ 7.34 (d, 1H); 7.28-7.12 (m, 6H); 4.62 (s, 2H); 4.12 (t, 1H); 2.98 (m, 2H); 2.80 (m, 1H); 2.34 (m, 2H); 2.14 (m, 2H); 1.32 (dd, 6H); 0.92 (dd, 12H).

By proceeding analogously, starting from (S)-2-(3-Diisopropylamino-1-phenyl-propyl)-4-hydroxymethyl-phenol, isobutyric acid (S)-2-(3-diisopropylamino-1-phenyl-propyl)-4-hydroxymethyl-phenyl ester is obtained.

EXAMPLE 7

Synthesis of isobutyric acid R-(+)-2-(3-diisopropylamino-1-phenyl-propyl)-4-hydroxymethyl-phenyl ester (Fesoterodine)

R-(+)-2-(3-Diisopropylamino-1-phenyl-propyl)-4-hydroxymethyl-phenol (2.5 g, 7.3 mmol) is dissolved in dimethylacetamide (10 ml) in a round-bottom flask under inert atmosphere and 90% potassium hydroxide (0.46 g, 7.3 mmol) is added thereto. The mixture is left under stirring for 3 hours until color changes to blue, then the mixture is dried by distillation under reduced pressure. After that, a solution of isobutyryl chloride (0.82 g, 7.7 mmol) in dimethylacetamide (10 ml) is slowly added, keeping stirring for 15 minutes. The reaction mixture is poured in water (100 ml) and extracted with toluene (50 ml), the phases are separated and the organic phase is washed with water (2×20 ml). The organic solution is concentrated under reduced pressure to afford a pale yellow oil, 2.7 g, in 91% yield.

By proceeding analogously, starting from (S)-2-(3-Diisopropylamino-1-phenyl-propyl)-4-hydroxymethyl-phenol, isobutyric acid (S)-2-(3-diisopropylamino-1-phenyl-propyl)-4-hydroxymethyl-phenyl ester is obtained.

The invention claimed is:

1. A process for the preparation of a compound of formula (IIa) or (IIb), or a salt thereof

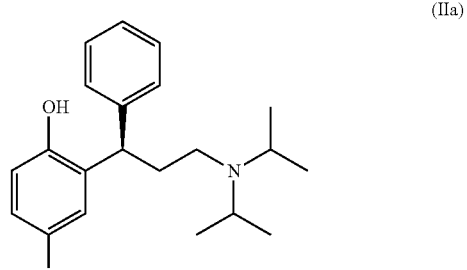

(IIa)

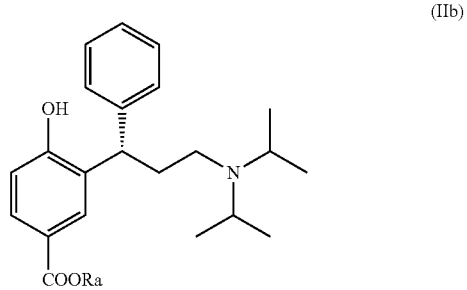

(IIb)

wherein Ra is a $C_1$-$C_6$ alkyl,
comprising the resolution of the corresponding racemic compound of formula (II)

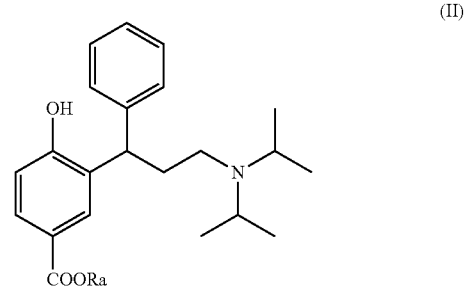

(II)

wherein Ra is as defined above, through formation of the diastereomeric salt thereof with an optically active organic acid.

2. The process of claim 1 wherein an optically active acid is an optically active carboxylic or sulfonic acid.

3. The process of claim 2 wherein the optically active acid is selected from (+) tartaric acid, (−) tartaric acid, (+) 2,3-dibenzoyl-tartaric acid, (−) 2,3-dibenzoyl-tartaric acid, mandelic acid, 3-chloromandelic acid, abietic acid, and S-(+)-camphorsulfonic acid.

4. The process of to claim 1, wherein the resolution of the racemic compound of formula (II) is carried out in a solvent selected from water, a dipolar aprotic solvent, a $C_3$-$C_8$ ketone, a cyclic or acyclic ether, an ester, a chlorinated solvent and a polar protic solvent, or a mixture of two or more of said solvents.

5. The process of claim 1, further comprising:
a) the reduction of the carboxylate group in a compound of formula (IIa) or of formula (IIb), or a salt thereof, as defined in claim 1, to obtain a compound of formula (IIIa) or (IIIb), respectively, or a salt thereof,

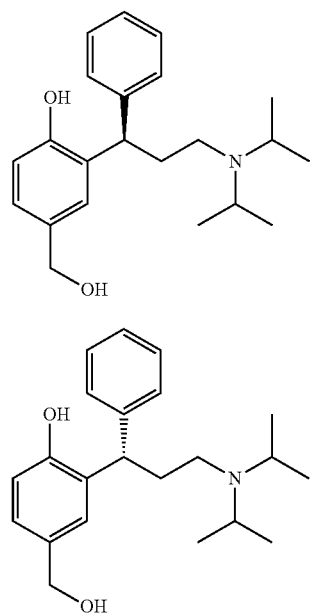

(IIIa)

(IIIb)

b) the esterification of the phenol hydroxyl group of a compound of formula (IIIa) or of formula (IIIb), or a salt thereof, to obtain Fesoterodine or its (S)-enantiomer, respectively; and, if desired, the conversion of Fesoterodine or its (S)-enantiomer into a pharmaceutically acceptable salt thereof, or the cleavage of a salt of Fesoterodine or of its (S)-enantiomer into free Fesoterodine or its (S)-enantiomer, respectively.

6. A process for the preparation of a compound of formula (IIa) or (IIb), or a salt thereof

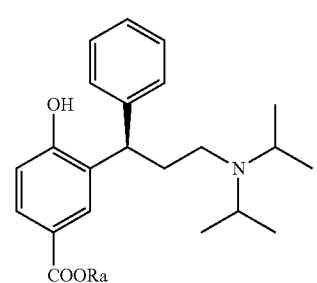

(IIa)

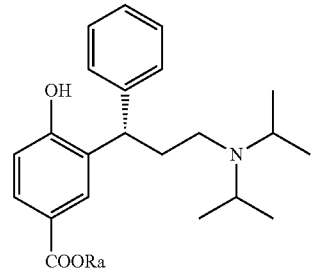

(IIb)

wherein Ra is a $C_1$-$C_6$ alkyl,
comprising resolving the corresponding racemic compound of formula (II)

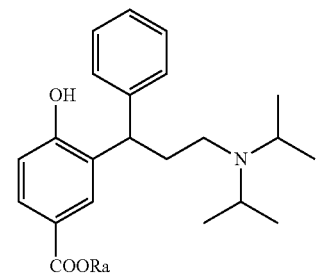

(II)

wherein Ra is as defined above, through formation of the diastereomeric salt thereof with an optically active organic acid, and further comprising:
a) reducing the carboxylate group in a compound of formula (IIa) or of formula (IIb), or a salt thereof, as defined in claim 1, to obtain a compound of formula (IIIa) or (IIIb), respectively, or a salt thereof,

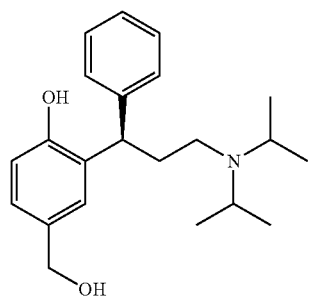

(IIIa)

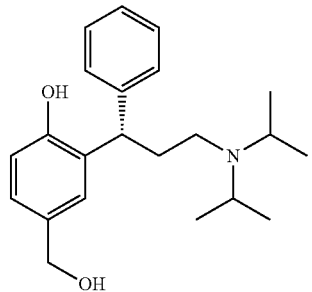

(IIIb)

b) esterifying the phenol hydroxyl group of a compound of formula (IIIa) or of formula (IIIb), or a salt thereof, to obtain Fesoterodine or its (S)-enantiomer, respectively; and, if desired, the conversion of Fesoterodine or its (S)-enantiomer into a pharmaceutically acceptable salt thereof, or the cleavage of a salt of Fesoterodine or of its (S)-enantiomer into free Fesoterodine or its (S)-enantiomer, respectively, wherein the esterification of the phenol hydroxyl group in a compound of formula (IIIa) or (IIIb), or a salt thereof, is carried out by a process comprising:
a) the treatment of a compound of formula (IIIa) or (IIIb), respectively, or a salt thereof, with an acylating agent under phase-transfer reaction conditions; or
b) the treatment of a compound of formula (IVa) or (IVb), respectively,

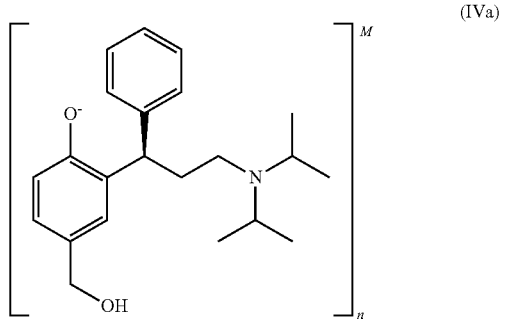

(IVa)

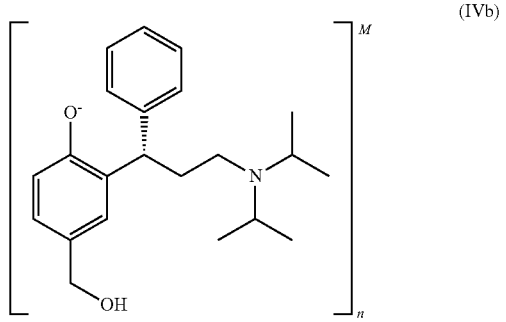

(IVb)

wherein M is an organic cation or an alkaline or alkaline-earth metal cation; and n is 1 or 2, with an acylating agent.

7. The process of claim 6, wherein the acylating agent is an isobutyryl halide.

8. The process of claim 7, wherein the isobutyryl halide is isobutyryl chloride or isobutyric anhydride.

9. The process of claim 6 wherein the reaction of a compound of formula (IVa) or (IVb) with an acylating agent is carried out in the presence of a solvent selected from water, a dipolar aprotic solvent, a $C_3$-$C_8$ ketone, a cyclic or acyclic ether, and a chlorinated solvent; or a mixture of two or more of said solvents.

10. The process of claim 1, further comprising the preparation of a compound of formula (II), or a salt thereof, by a process comprising the reaction of a compound of formula (V)

(V)

wherein Ra is as defined in claim 1; with a compound of formula (VI), or a salt thereof,

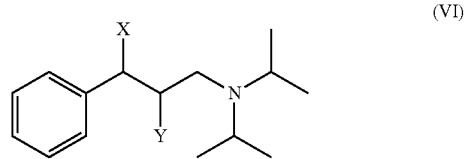

(VI)

wherein X is a group capable of generating a benzyl carbocation and Y is hydrogen, or X and Y, taken together, form a double bond; in the presence of a strong acid.

11. The process of claim 10, wherein the strong acid is a strong protic acid or a Lewis acid.

12. The process of claim 11, wherein the acid is selected from hydrochloric, sulfuric, hydrobromic, perchloric, polyphosphoric, trifluoroacetic, methanesulfonic, p-toluenesulfonic, trifluoromethanesulfonic acid, $AlCl_3$, $FeCl_3$, and $BF_3$ etherate.

13. The process of claim 10, wherein the molar ratio of a compound of formula (V) to a compound of formula (VI), or a salt thereof, is comprised between 1:1 and 8:1.

14. A process for preparing Fesoterodine or its (S)-enantiomer, or a salt thereof, comprising obtaining a compound of formula (IIa) or (IIb), or a salt thereof

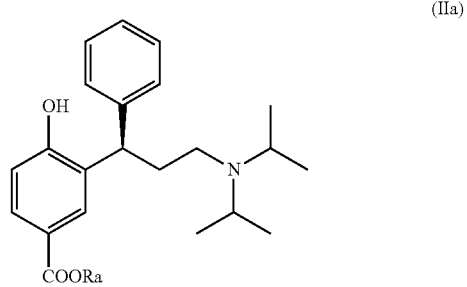

(IIa)

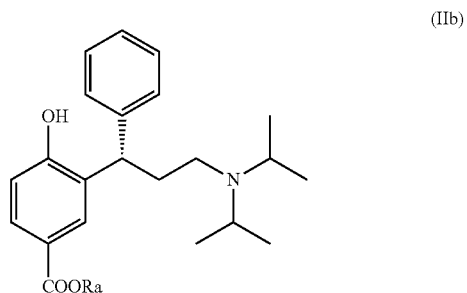

(IIb)

wherein Ra is a $C_1$-$C_6$ alkyl, by the resolution of a corresponding racemic compound of formula (II)

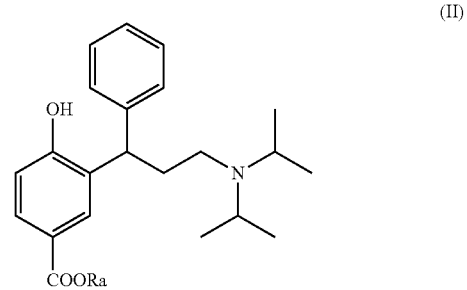

(II)

wherein Ra is as defined above, through formation of a diastereomeric salt thereof with an optically active organic acid.

15. The process of claim 4, wherein the resolution of the racemic compound of formula (II) is carried out in a mixture of at least two solvents selected from the group consisting of water, a dipolar aprotic solvent, $C_3$-$C_8$ ketone, a cyclic or acyclic ether, an ester, a chlorinated solvent and a polar protic solvent.

* * * * *